(12) United States Patent
Liu et al.

(10) Patent No.: US 11,790,574 B2
(45) Date of Patent: Oct. 17, 2023

(54) SYSTEM AND METHOD FOR CARBON DIOXIDE ANGIOGRAPHIC ROADMAP IMAGING

(71) Applicant: GE Precision Healthcare LLC, Wauwatosa, WI (US)

(72) Inventors: James Liu, Cottonwood Heights, UT (US); Naveen S. Chandra, Salt Lake City, UT (US); Jon T. Lea, Salt Lake City, UT (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 145 days.

(21) Appl. No.: 17/101,820

(22) Filed: Nov. 23, 2020

(65) Prior Publication Data
US 2022/0165000 A1 May 26, 2022

(51) Int. Cl.
G06T 11/00 (2006.01)
A61B 6/12 (2006.01)
A61B 6/00 (2006.01)
A61K 49/04 (2006.01)
G06T 7/00 (2017.01)

(52) U.S. Cl.
CPC .............. *G06T 11/001* (2013.01); *A61B 6/12* (2013.01); *A61B 6/504* (2013.01); *A61B 6/5205* (2013.01); *A61K 49/04* (2013.01); *G06T 7/0012* (2013.01); *G06T 2207/10116* (2013.01); *G06T 2207/30101* (2013.01)

(58) Field of Classification Search
CPC .......... G06T 11/00; G06T 7/0012; A61B 6/12
See application file for complete search history.

(56) References Cited

U.S. PATENT DOCUMENTS

| 8,509,384 B2 | 8/2013 | Spahn | |
|---|---|---|---|
| 2009/0180591 A1* | 7/2009 | Baumgart | A61B 6/463 600/407 |
| 2009/0279767 A1 | 11/2009 | Kukuk | |

(Continued)

OTHER PUBLICATIONS

A. Gupta et al, "Carbon dioxide-angiography for patients with peripheral arterial disease at risk of contrast-induced nephropathy," Would Journal of Cardiology, 12(2):76-90, Feb. 2020, 15 pages.

(Continued)

*Primary Examiner* — John Villecco
*Assistant Examiner* — Courtney Joan Nelson (57) ABSTRACT

The present disclosure relates to systems and methods for visualizing a guidewire in a roadmap image. In accordance with certain embodiments, a method includes generating a background mask as a function of at least one background image, wherein the at least one background image includes a blood vessel of interest, generating a contrast mask as a function of at least one contrast image, wherein the at least one contrast image includes a contrast within the blood vessel of interest, receiving a guidewire image, wherein the guidewire image includes a guidewire within the blood vessel of interest, generating a roadmap image as a function of the background mask, contrast mask, and guidewire image, wherein the roadmap image includes the blood vessel of interest, and the guidewire, and outputting the roadmap image to a display.

14 Claims, 5 Drawing Sheets

(56) References Cited

U.S. PATENT DOCUMENTS

| | | | |
|---|---|---|---|
| 2011/0038458 A1* | 2/2011 | Spahn | A61B 6/588 378/98.12 |
| 2015/0196260 A1* | 7/2015 | Lee | A61B 6/487 600/424 |
| 2016/0228084 A1* | 8/2016 | Nempont | A61B 6/504 |
| 2020/0020100 A1* | 1/2020 | Kyriakou | G06T 7/12 |

OTHER PUBLICATIONS

B. Funaki, "Carbon Dioxide Angiography," Seminars in Interventional Radiology, 25(1): 65-70, Feb. 2011, 6 pages.

Cho, "Carbon Dioxide Angiography: Scientific Principles and Practice," Vascular Specialist International, 31(3): 67-80, Sep. 2015, 14 pages.

J. G. Caridi et al, "Carbon Dioxide Digital Subtraction Angiography (CO2 DSA): A Comprehensive User Guide for All Operators," Vascular Disease Management, pp. 221-256, Oct. 2014, 36 pages.

J. G. Caridi, "Vascular Imaging with Carbon Dioxide" Confidence in a Safe, Efficacious, User-Friendly System, Seminars in Interventional Radiology, 32(4):339-342, Nov. 2015, 5 pages.

J. M. Moos et al, "Safety of Carbon Dioxide Digital Subtraction Angiography," Arch Surg., 146 (12): 1428-1432, Dec. 2011, 5 pages.

K. S. Madhusudhan et al, "Comparison of intra-arterial digital subtraction angiography using carbon dioxide by 'home made' delivery system and conventional iodinated contrast media in the evaluation of peripheral arterial occlusive disease of the lower limbs," Journal of Medical Imaging and Radiation Oncology, 53: 40-49, 2009, 20 pages.

S. R. Kerns et al, "Carbon Dioxide Digital Subtraction Angiography: Expanding Applications and Technical Evolution," American Journal of Radiology, 164:735-741, Mar. 1995, 12 pages.

Sharafuddin et al., "Current status of carbon dioxide angiography," Journal of Vascular Surgery, 66(2): 618-637, Mar. 2017, 20 pages.

Yang et al, "Carbon Dioxide in Vascular Imaging and Intervention," Acta Radiologica, 36: 330-337, 1995, 9 pages.

EP application 21208028.7 filed Nov. 12, 2021—Extended Search Report dated May 11, 2022, 8 pages.

* cited by examiner

SYSTEM AND METHOD FOR CARBON DIOXIDE ANGIOGRAPHIC ROADMAP IMAGING

TECHNICAL FIELD

This disclosure relates to systems and methods for visualizing a guidewire in a roadmap image based on digital subtraction angiography and more particular to systems and methods for visualizing a guidewire in a roadmap image based on carbon dioxide digital subtraction angiography.

BACKGROUND

Interventional cardiology involves detecting, clearing, and/or stenting coronary arteries that have become obstructed due to the buildup of plaque on the walls of the arteries. When a coronary artery becomes blocked, a surgeon may attempt to clear and/or stent the occlusion by performing a retrograde navigation within the artery. A retrograde navigation involves introducing a guidewire into a non-blocked artery and navigating the guidewire antegrade within a non-blocked artery, through a collateral artery that connects the non-blocked artery and the blocked artery, and entering into the distal end of the blocked artery in order to approach the occlusion from the downstream side. After the guidewire reaches its destination, the guidewire serves as a guide for a larger catheter (i.e., a balloon catheter) which is then used to complete the procedure. An angiogram may be used to visualize the guidewire as it is moved through the body.

SUMMARY

In one embodiment, the present disclosure provides a method. The method includes generating a background mask as a function of at least one background image, wherein the at least one background image includes a blood vessel of interest; generating a contrast mask as a function of at least one contrast image, wherein the at least one contrast image includes a contrast within the blood vessel of interest; receiving a guidewire image, wherein the guidewire image includes a guidewire within the blood vessel of interest; generating a roadmap image as a function of the background mask, contrast mask, and guidewire image, wherein the roadmap image includes the blood vessel of interest, and the guidewire; and outputting the roadmap image to a display.

In another embodiment, the present disclosure provides s system. The system includes an X-ray imaging device; a processor; and a computer readable storage medium in communication with the processor. When the processor executes computer readable instructions stored in the computer readable storage medium the instructions cause the processor to: generate a background mask as a function of at least one background image generated by the X-ray imaging device, wherein the at least one background image includes a blood vessel of interest; generate a contrast mask as a function of at least one contrast image generated by the X-ray imaging device, wherein the at least one contrast image includes a contrast within the blood vessel of interest; receive a guidewire image generated by the X-ray imaging device, wherein the guidewire image includes a guidewire within the blood vessel of interest; generate a roadmap image as a function of the background mask, contrast mask, and guidewire image, wherein the roadmap image includes the blood vessel of interest, and the guidewire; and output the roadmap image to a display.

In yet another embodiment, the present disclosure provides a computer readable storage medium with computer readable instructions. When the processor executes the computer readable instructions, the instructions cause the processor to: generate a live roadmap image as a function of a background mask that includes a background of a blood vessel of interest, a contrast mask that includes a contrast agent within the blood vessel of interest, and a live guidewire image; and output the roadmap image to a display.

BRIEF DESCRIPTION OF THE DRAWINGS

Various aspects of this disclosure may be better understood upon reading the following detailed description with reference to the drawings in which.

The drawings illustrate specific acts of the described components, systems, and methods for visualizing a guidewire in a roadmap image. Together with the following description, the drawings demonstrate and explain the structures, methods, and principles described herein. In the drawings, the thickness and size of components may be exaggerated or otherwise modified for clarity. Well-known structures, materials, or operations are not shown or described in detail to avoid obscuring aspects of the described components, systems, and methods.

DETAILED DESCRIPTION

One or more specific embodiments of the present disclosure are described below. These described embodiments are only examples of the systems and methods for visualizing a guidewire in a roadmap image. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

While performing an interventional cardiology procedure it is vital to clearly observe the guidewire as it moves through the body. As previously discussed, an angiogram may be used to visualize a guidewire while it moves through an artery. During an angiogram imaging procedure, a patient is injected with a contrast agent that is visible when X-rayed. The contrast agent aids in contrasting the guidewire from a background of the image and/or an artery that contains the guidewire.

Some angiography procedures for guidewire viewing use iodine as a contrast and include digitally subtracting a fluoroscopic image from an earlier generated image (or mask) of the same region. In the fluoroscopic image the guidewire is dark and in the previously generated mask blood vessels appear dark as well. After subtraction, background and bony structure in both the fluoroscopic image and the mask are canceled out and the dark blood vessels are inversed to white. Thus, the guidewire appears as dark and the blood vessels appear as white in a fluoroscopic image that depicts the guidewire in a blood vessel. The guidewire within the blood vessel may be displayed to a surgeon performing the interventional cardiology procedure in the form of a roadmap image. As used herein, a roadmap image includes a live fluoroscopic image that is superimposed on or otherwise combined with a previously generated digitally subtracted angiogram. Accordingly, a roadmap image based on iodinated digital subtraction angiography (an "iodinated angiographic roadmap" based on "iodinated DSA") clearly displays the guidewire and blood vessel as the guidewire and blood vessel contrast.

Unfortunately, iodine is not a suitable contrast agent for all patients. For example, iodine cannot be used for patients with renal failure or hypersensitivity to iodine. In such cases, carbon dioxide ($CO_2$) may be alternatively used as a contrast agent. When $CO_2$ is injected into a blood vessel, the $CO_2$ replaces blood which results in a lower X-ray attenuation. Unfortunately, current roadmap images wherein the contrast agent is $CO_2$ are generated using the same procedure as iodinated contrast agents and as a result, $CO_2$ roadmap images are not optimal as both blood vessel and guidewire appear as either dark or white rendering it difficult to view the guidewire. Thus, there is a need for a method and/or a system that generates a $CO_2$ angiographic roadmap wherein the guidewire and blood vessel contrast from one another.

Figure 1:
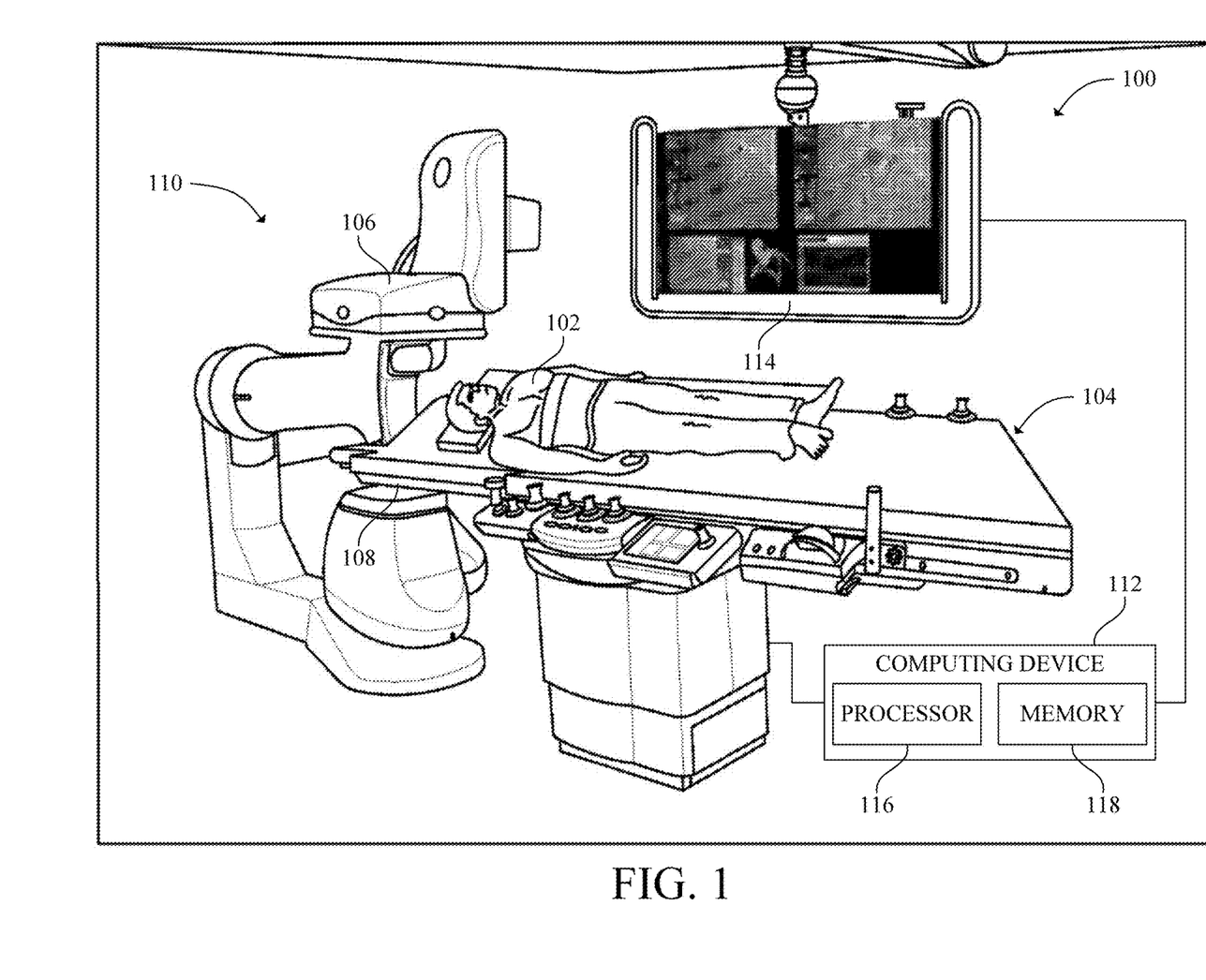
FIG. 1 depicts an imaging system in accordance with an exemplary embodiment.

Referring to the figures generally, the present disclosure describes systems and methods for visualizing a guidewire in a $CO_2$ angiographic roadmap image. While the embodiments herein are described with respect to an X-ray fluoroscopic imaging system (i.e., an X-ray angiographic imaging system as depicted in FIG. 1), it is understood that other embodiments may include other devices such as computed tomography ("CT") imaging systems, positron emission tomography ("PET") systems, real-time endoscopic imaging systems, and/or other imaging systems that utilize a contrast agent. It is further understood that embodiments described herein may be used to analyze objects within any material which can be internally imaged. As such, embodiments disclosed herein are not limited to analyzing objects with human tissue.

While the embodiments disclosed herein are described with respect to an X-ray based fluoroscopic imaging system (as shown in FIG. 1), it is to be understood that embodiments of the present invention are equally applicable to other devices such as Computed Tomography ("CT") X-ray imaging systems, Magnetic Resonance Imaging ("MRI") systems, Positron Emission Tomography ("PET"), real-time endoscopic imaging, and/or any other type of imaging systems that utilize $CO_2$ as a contrast agent. As will be appreciated, embodiments of the present invention related imaging systems may be used to analyze objects within any material which can be internally imaged, generally. As such, embodiments of the present invention are not limited to analyzing objects within human tissue.

Referring now to FIG. 1, an imaging system 100 is shown in accordance with an exemplary embodiment. In one embodiment, the imaging system 100 is an X-ray angiographic imaging system. While FIG. 1 depicts a stationary c-arm imaging system 100, in a second embodiment, the imaging system 100 may be a mobile c-arm imaging system. In yet another embodiment, the imaging system 100 may be a non c-arm imaging system. The imaging system 100 is operative to image one or more structures (i.e., an internal organ, blood vessel, etc.) within a patient 102. For example, the patient 102 may be suffering from one or more blocked coronary arteries and the imaged structures may be the one or more blocked coronary arteries. As illustrated in FIG. 1, in some embodiments, the imaging system 100 includes a patient support 104 adapted to support the patient 102 while the patient 102 is being imaged, a radiation source 106, and a radiation sensitive detector 108. Collectively, the radiation patient support 104, the radiation source 106, and the radiation sensitive detector array 108 form imaging device 110. In one embodiment, the imaging device 110 is an X-ray angiographic imaging device.

The imaging system 100 further includes a computing device 112, and a display 114. As used herein, a computing device is any device/system capable of processing and transmitting data (i.e., tablet, handheld computing device, smart phone, personal computer, laptop, network computer, server, mobile communication device, etc.). While the computing device 112 and display 114 are depicted as separate from the imaging device 110, in some embodiments, the imaging device 110 may include the computing device 112 and the display 114.

The computing device 112 is connected to and in communication with the imaging device 110 and the display 114 via a wired or wireless connection thereby allowing computing device 112 to transmit data to/receive data from the imaging device 110 and output an image and/or a video to the display 114. The imaging device 110 and the computing device 112 may be connected to a network (i.e., a wide area network (WAN), a local area network (LAN), a public network (the Internet), etc.) which allows the imaging device 110 and the computing device 112 to communicate with one another when connected to a same network. In some embodiments, the network may be regarded as a private network connection and may include, for example, a virtual private network or an encryption or other security mechanism employed over the public Internet. In one embodiment, the computing device 112 may be remotely located with respect to the imaging device 110. In another embodiment, the computing device 112 may be located in a same room as the imaging device 110.

The computing device 112 includes a processor 116 and a system memory 118. The processor 116 is in communication with the system memory 118 and may execute computer readable program instructions stored in the system memory 118. In one embodiment, a processor may include a central processing unit (CPU). In another embodiment, a processor may include other electronic components capable of executing computer readable program instructions, such as a digital signal processor, a field-programmable gate array (FPGA), or a graphics board. In yet another embodiment, a processor may be configured as a graphics processing unit (GPU) with parallel processing capabilities. In yet another embodiment, a processor may include multiple electronic components capable of carrying out computer readable instructions. For example, a processor may include two or more electronic components selected from a list of electronic components including: a CPU, a digital signal processor, an FPGA, and a GPU.

The system memory 118 is a computer readable storage medium. As used herein a computer readable storage medium is any device that stores computer readable program instructions for execution by a processor and is not construed as being transitory per se. Computer readable program instructions include programs, logic, data structures, modules, architecture etc. that when executed by a processor create a means for implementing functions/acts. Computer readable program instructions when stored in a computer readable storage medium and executed by a processor direct a computer system and/or another device to function in a particular manner such that a computer readable storage medium comprises an article of manufacture. System memory as used herein includes volatile memory (i.e., random access memory (RAM) and dynamic RAM (DRAM)) and nonvolatile memory (i.e., flash memory, read-only memory (ROM), magnetic computer storage devices, etc.). In some embodiments, the system memory may further include cache.

The display 114 displays a graphical user interface (GUI). As used herein, a GUI includes editable data (i.e., patient data) and/or selectable icons. A user may use an external device (i.e., keyboard, mouse, touch screen, etc.) connected to the computing device 112 to select an icon and/or edit the data. Selecting an icon/entering information causes a processor to execute computer readable program instructions stored in a computer readable storage medium which cause the processor to perform various tasks. For example, a user may use an external device to select an icon which causes the processor 116 to control the medical imaging device 110 to carry out an imaging session. As used herein, an imaging session includes acquisition/generation of a plurality of medical images including angiogram images of a blood vessel of interest.

Figure 2:
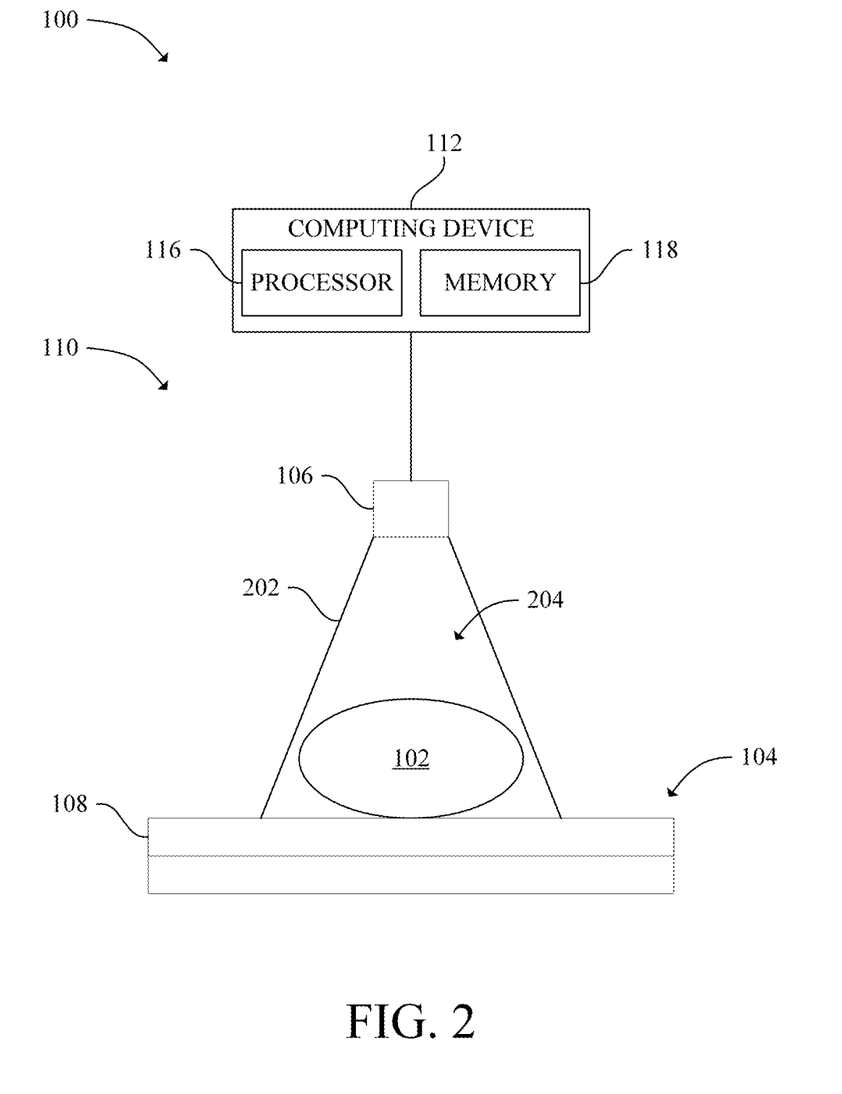
FIG. 2 is a block diagram of an imaging system in accordance with an exemplary embodiment.

Referring now to FIG. 2, a block diagram of the imaging system 100 is shown in accordance with an exemplary embodiment.

When the processor 116 executes computer readable program instructions to begin a medical imaging procedure, the processor 116 sends a signal to the radiation source 106 to emit radiation. In some embodiments, the radiation source 106 is an X-ray tube. In response, the radiation source 106 emits radiation 202 that traverses an examination region 204. The radiation sensitive detector 108 detects the radiation 202 that has traversed the examination region 204 and has been attenuated by the patient 102. In response to detecting the radiation 202, the radiation sensitive detector generates projection data. The intensity of the detected radiation is dependent upon the attenuation by the patient 102. The radiation sensitive detector 108 includes elements that each produce separate electrical signal that is a measurement of the attenuation at the element location. The attenuation measurements from all the detector elements are acquired separately to produce a transmission profile.

The imaging device 110 sends the projection data to the computing device 112. In response to receiving the projection data, the processor 116 may execute computer readable program instructions stored in the system memory 118 to processes the projection data to reconstruct an image and/or a video. As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. Once reconstruction is complete, the processor 116 may output the reconstructed image/video to the display 114 in the form of image data.

In one embodiment, wherein the processor 116 outputs a video to the display 114, the video may include a plurality of composite images/frames. The term "composite image", as used herein, means an image generated from two or more other images. For instance, in embodiments, a single composite image may be generated by registering one or more live images to an earlier acquired mask. In some embodiments a video feed output to the display 114 may be a live/real-time and/or near-real-time feed.

In one embodiment, the medical imaging procedure is an angiography imaging procedure of a blood vessel of interest. An angiography imaging procedure includes injecting a contrast agent (i.e., $CO_2$) into the blood vessel of interest or into a blood vessel that is upstream of the blood vessel of interest. During an angiography imaging procedure, an imaging device (i.e., the imaging device 110) continuously captures projection data and a processor (i.e., the processor 116) outputs reconstructed images (based on the projection data) to a display (i.e., the display 114) in real-time.

The contrast agent causes the lumen of the blood vessel of interest to have a different attenuation value than an area that surrounds the blood vessel of interest (i.e., a background of the blood vessel of interest). For example, when the contrast agent is $CO_2$ or another contrast agent that displaces blood within a blood vessel of interest, the contrast agent causes the lumen of the blood vessel of interest to have a lower attenuation value than a background of the blood vessel of interest. Since the blood vessel with the contrast agent has a different attenuation value than the background, processor may output images to the display wherein the blood vessel of interest is visible. Stated another way, during an angiography imaging procedure, a processor outputs a live video of a blood vessel of interest based on projection data captured by an imaging device, wherein the blood vessel of interest is visible. Stated yet another way, during an angiography imaging procedure, a processor outputs a live fluoroscopic image of a blood vessel of interest based on projection data captured by an imaging device, wherein the blood vessel of interest is visible.

In one embodiment, wherein the imaging procedure is an angiography imaging procedure of a blood vessel of interest, the angiography imaging procedure may be performed during an interventional procedure that includes inserting a guidewire into the blood vessel of interest. The guidewire may have a different attenuation value than the blood vessel with the contrast agent and/or the background of the blood vessel of interest. In this embodiment, during the angiography imaging procedure, the processor may output images/a live video/a live fluoroscopic image wherein the blood vessel of interest and the guidewire is visible.

In another embodiment, wherein the imaging procedure is an angiography imaging procedure of a blood vessel of interest that is performed during an interventional procedure that includes inserting a guidewire into the blood vessel of interest, an imaging device may capture projection data of the blood vessel of interest before the angiography imaging procedure. A processor may reconstruct the previously captured image data to form a mask image of the blood vessel of interest. During the angiography imaging procedure that is performed while a guidewire is in the blood vessel of interest, the processor may reconstruct an image from projection data captured during the angiography imaging procedure and subtract the mask from the image generated during the angiography imaging procedure to form a roadmap image. The processor may output the roadmap image to a display as a plurality of images or a live video.

Figure 3:
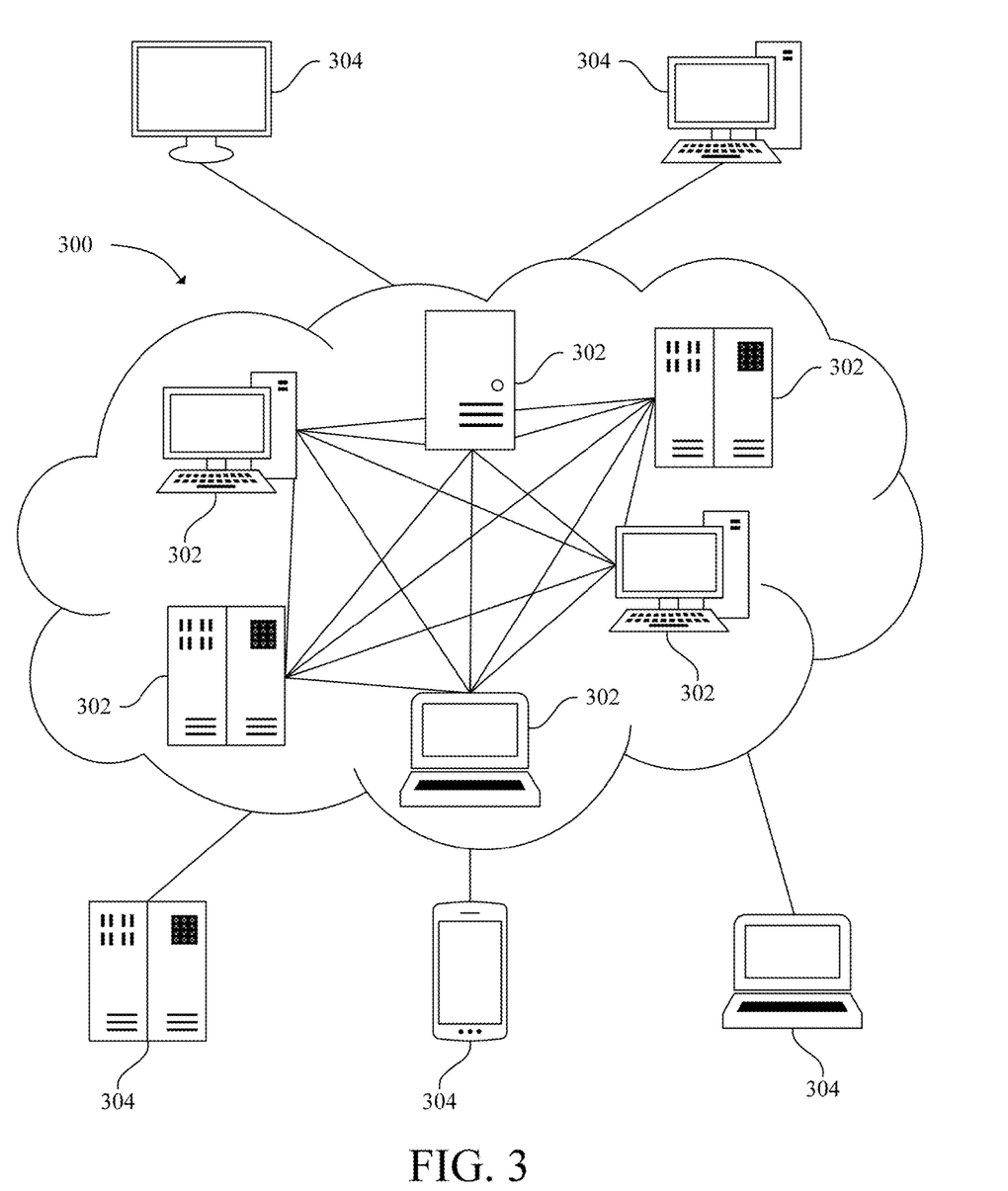
FIG. 3 depicts a cloud computing environment in accordance with an exemplary embodiment.

Referring now to FIG. 3 a cloud computing environment 300 is shown in accordance with an exemplary embodiment. As illustrated in FIG. 3, in some embodiments, the cloud computing environment 300 includes one or more nodes 302. Each node 302 may include a computer system/server (i.e., a personal computer system, a server computer system, a mainframe computer system, etc.). The nodes 302 may communicate with one another and may be grouped into one or more networks. Each node 302 may include a computer readable storage medium and a processor that executes instructions in the computer readable storage medium. As further illustrated in FIG. 3 one or more devices (or systems) 304 may be connected to the cloud computing environment 300. The one or more devices 304 may be connected to a same or different network (i.e., LAN, WAN, public network, etc.). One or more nodes 302 may communicate with the devices 304 thereby allowing the nodes 302 to provide software services to the devices 304. In one embodiment, a node 302 may include the computing device 112. In another embodiment, a device 304 may include the computing device 112.

Figure 4:
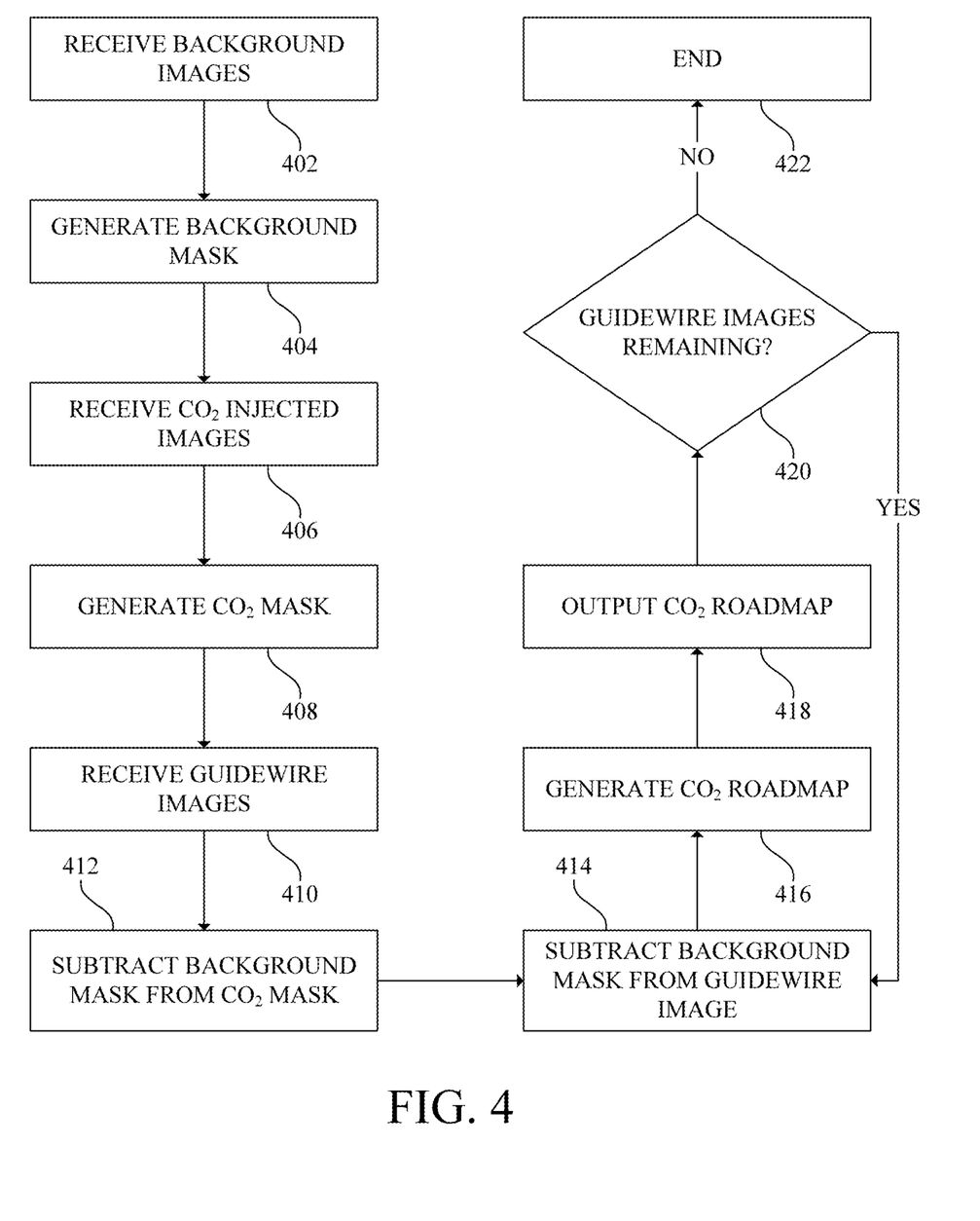
FIG. 4 is a flow chart of a method for visualizing a guidewire in a roadmap image in accordance with an exemplary embodiment.

Referring now to FIG. 4, a flow chart of a method 400 for visualizing a guidewire in an angiographic roadmap is shown in accordance with an exemplary embodiment. Various aspects of the method 400 depicted in FIG. 4 may be carried out by a "configured processor." As used herein, a configured processor is a processor that is configured according to an aspect of the present disclosure. A configured processor(s) may be the processor 116, a processor of a node 302, or a processor of a device 304. A configured processor executes various computer readable program instructions to perform the steps of the method 400. The computer readable program instructions, that when executed by a configured processor, cause a configured processor to carry out the steps of the method 400 are stored in a computer readable storage medium including, but not limited to, the system memory 118, a system memory of a node 302, or a system memory of a device 304. When performed by a configured processor, the steps of the method 400 cause the configured processor to output an angiographic roadmap image wherein a blood vessel contrasts with respect to a guidewire within the blood vessel. While the method 400 implements $CO_2$ as the contrast agent to generate the roadmap, it is understood that other negative contrast agents (i.e., oxygen, etc.) may be used to generate the roadmap At 402, the configured processor receives a sequence of background images $\{I_{Background}(l), l=1, 2, \ldots, L\}$. In some embodiments, the background images are generated by the imaging system 100. The background images include the bony structure, tissue structure, and a blood vessel of interest filled with blood. The imaging system 100 generates the background images during an imaging session, wherein no contrast (i.e., $CO_2$ contrast) or guidewire is present in the blood vessel of interest. For example, during an imaging session, the imaging system 100 may generate sixteen images of a blood vessel of interest of the patient 102 during an imaging session that does not include a $CO_2$ contrast nor a guidewire. Accordingly, in this example, $\{I_{Background}(l), l=1-16\}$.

At 404, the configured processor generates a background mask image ($M_{Background}$). The configured processor generates $M_{Background}$ by temporally averaging the image data (i.e., pixel values) of the received background images acquired with no contrast injection nor any object being inside the blood vessel. As such, the configured processor may generate $M_{Background}$ as a function of EQUATION 1:

$$M_{Background} = \frac{1}{L}\sum_{l=1}^{L} I_{Background}(l)$$

At 406, the configured processor receives a sequence of $CO_2$ injected images $\{I_{CO2}(k), k=1, 2, \ldots, K\}$. Since the x-ray attenuation of $CO_2$ is smaller than the X-ray attenuation of blood, these $CO_2$ injected images can be considered as if the blood vessel is empty. In one example, the configured processor receives 120 contrast agent injected images. Accordingly, in this example, $\{I_{CO2}(k), k=1-120\}$. In one embodiment, the sequence of $CO_2$ injected images and the sequence of background images are generated by the imaging system 100 during a same imaging session. In another embodiment, the imaging system 100 generates the sequence of $CO_2$ injected images and the sequence of background images during different imaging sessions. The sequence of $CO_2$ injected images includes the blood vessel of interest through peak opacification of $CO_2$ within the blood vessel of interest. In some embodiments, the first image in the sequence of $CO_2$ injected images, the blood vessel of interest does not include any injected $CO_2$ within the blood vessel of interest. That is, the first image may have been acquired before the injected $CO_2$ arrives at the blood vessel of interest.

At 408, the configured processor generates a $CO_2$ mask image ($M_{CO2}$) as a function of the $CO_2$ injected images. The configured processor generates $M_{CO2}$ according to EQUATION 2:

$$M_{CO2} = CO2\_Peak\_Opacification[I_{CO2}(k), k=1, 2, \ldots, K]$$

where the $CO_2$ peak opacification is the operation of finding the most positive pixel value for each of the pixel locations over the K $CO_2$ injected images $\{I_{CO2}(k), k=1, 2, \ldots, K\}$.

At 410, the configured processor receives a sequence of live guidewire images $\{F_{GWire}(n), n=1, 2, \ldots, N\}$ (or "a set of guidewire images"). The guidewire images include a guidewire within the blood vessel of interest. In one embodiment, the set of guidewire images is generated by the imaging system 100. In this embodiment, the imaging system 100 generates the guidewire images as the guidewire is moved through the blood vessel of interest. In one example, the configured processor receives three hundred guidewire images. That is, during an imaging session, the imaging device 110 generates three hundred guidewire images. Accordingly, in this example, $\{F_{GWire}(n), n=1-300\}$. In some embodiments, the number N guidewire image is the last image acquired/reconstructed during an angiography imaging procedure. In this embodiment, $\{F_{GWire}(n), n=1, 2, \ldots, N\}$ corresponds to a set of guidewire images acquired during an angiography imaging procedure. Furthermore, the number of guidewire images in the set of guidewire images may increase as an imaging procedure proceeds. That is, the number N image may correspond to a live image most recently generated by an imaging system.

At 412, the configured processor registers $M_{Background}$ and $M_{CO2}$ and subtracts $M_{Background}$ from $M_{CO2}$ in linear domain as a function of the registration according to EQUATION 3:

$$[\ln(M_{CO2}(M_{Background}))]$$

wherein the logarithm operation ln(•) transforms pixel values of the image into linear domain for subtraction. Since $M_{CO2}$ contains the empty blood vessel as well as the tissue and bony structures while $M_{Background}$ contains the blood filed blood vessel as well as the tissue and bony structures of the anatomy, $[\ln(M_{CO2})-\ln(M_{Background})]$ removes the background (e.g. tissue and bony structures as well as the blood filed blood vessel) and generates an image that contains only the blood vessel of interest. In one embodiment, the blood vessel of interest is white in $M_{CO2}$. In this embodiment, $[\ln(M_{CO2})-\ln(M_{Background})]$ contains only a white blood vessel of interest.

At 414, the configured processor registers $M_{Background}$ and a guidewire image in the set of guidewire images $F_{GWire}(n)$ and subtracts $M_{Background}$ from $F_{GWire}(n)$ in linear domain as a function of the registration according to EQUATION 4:

$$[\ln(F_{GWire}(n))-\ln(M_{Background})].$$

Since $F_{GWire}(n)$ contains the guidewire as well as the background and $M_{Background}$ contains only the background, $[\ln(F_{GWire}(n))-\ln(M_{Background})]$ removes the background and generates an image that contains only the guidewire. In one embodiment, the guidewire is a dark color (i.e., dark gray, black, etc.). In this embodiment, $[\ln(F_{GWire}(n))-\ln(M_{Background})]$ contains only a dark guidewire.

At 416, the configured processor generates a roadmap image (i.e., a $CO_2$ roadmap image). The configured processor generates the roadmap image by registering the generated image at 412 (the image that contains only the blood vessel of interest) and the image generated at 414 (image that contains only the guidewire) and super imposing (or otherwise combining) the image generated at 412 on the image generated at 414 as a function of the registration. As such, the roadmap image contains the blood vessel of interest and the guidewire.

In one embodiment, the configured processor may apply a weighting factor α to the images generated at 412 and 414 in order to balance the contrast between the blood vessel and the guidewire in the roadmap image. The weighting factor may be determined as a function of at least one patient parameter (i.e., a patient thickness, a patient weight, etc.) and be greater than 0 and less than 1 (0<α<1). Accordingly, in this embodiment, the configured processor generates the roadmap image according to EQUATION 5:

$$R_{MAP}(n)=(1-\alpha)[\ln(F_{GWire}(n))-\ln(M_{Background})]+\alpha[\ln(M_{CO2})-\ln(M_{Background})]$$

wherein $R_{MAP}(n)$ is the $CO_2$ roadmap image for image n in the set of guidewire images. In one embodiment, the weighting factor increases with a patient thickness or patient weight. For example, a first patient may be larger (i.e., has a thicker abdomen cross section) than a second patient. In this example a first weighting factor that corresponds to the first patient is greater than a second weighting factor that corresponds to the second patient.

While EQUATIONS 3-5 include performing a logarithmic linearization of $F_{GWire}(n)$, $M_{Background}$, and $M_{CO2}$, EQUATIONS 3-5 may linearize $F_{GWire}(n)$, $M_{Background}$, and $M_{CO2}$ by applying other functions (i.e., a polynomial function, a linear-logarithm function where linear function is used on smaller signal and logarithm function is used on larger signal, etc.) to $F_{GWire}(n)$, $M_{Background}$, and $M_{CO2}$.

Figure 5:
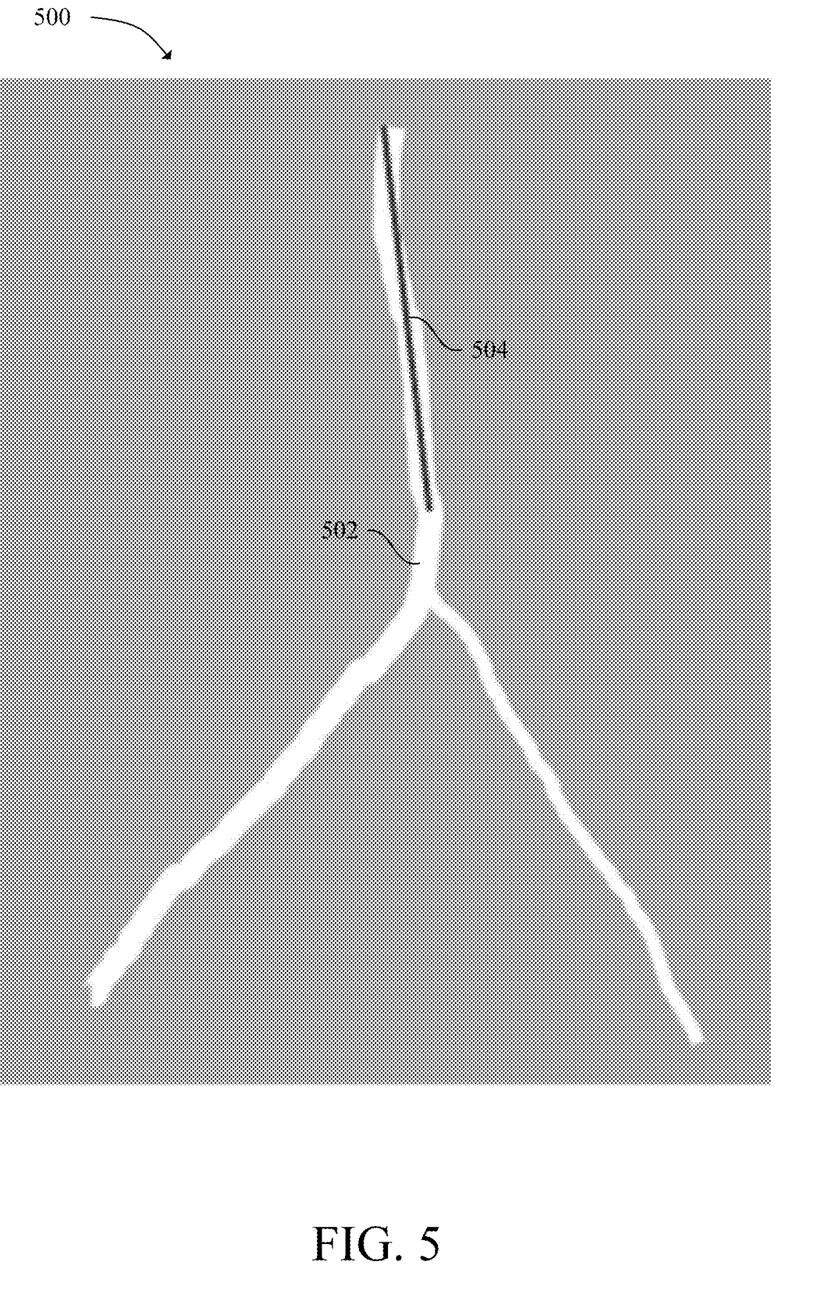
FIG. 5 depicts a roadmap image in accordance with an exemplary embodiment.

Briefly turning to FIG. 5, a roadmap image 500 is depicted in accordance with an exemplary embodiment. In one embodiment, the roadmap image 500 is generated at 416 and includes a blood vessel of interest 502 and a guidewire 504. Since, in some embodiments, $[\ln(M_{CO2})-\ln(M_{Background})]$ contains only a white blood vessel of interest and $[\ln(F_{GWire}(n))-\ln(M_{Background})]$ contains only a dark guidewire, the blood vessel of interest 502 may be white and the guidewire 504 may be dark. Due to this contrast, the method 400 may generate a roadmap image (i.e., a $CO_2$ roadmap image) wherein a guidewire is more visible.

Returning to FIG. 4, at 418, the configured processor outputs the $CO_2$ roadmap image to a display.

At 420, the configured processor determines if n=N on $F_{GWire}(n)$. Stated another way, at 420, the configured processor determines if the n'th image used to generate $R_{MAP}(n)$ is the last image in the set of guidewire images. As previously discussed, in some embodiments, $F_{GWire}(n)$ corresponds to a live image and as such, $F_{GWire}(N)$ may correspond to a last image in an imaging procedure.

In response to determining $F_{GWire}(n)$, n≠N, the configured processor repeats steps 414-418 for $F_{GWire}(n+1)$.

At 422, in response to determining $F_{GWire}(n)$, n=N the configured processor ends method 400. While FIG. 4 depicts method 400 proceeding in an ordered operation, any steps of the method 400 may occur simultaneously. For example, the configured processor may simultaneously perform steps 414-418. Also, the configured processor may output $R_{MAP}(N)$ immediately after the imaging device acquires $F_{GWire}(N)$ such that the configured processor outputs $R_{MAP}(N)$ as a live image. Furthermore, the configured processor may output a first roadmap image (i.e., $R_{MAP}(n)$) and immediately thereafter output a second roadmap image (i.e., $R_{MAP}(n+1)$) such that the configured processor outputs the roadmap images as a video.

In addition to any previously indicated modification, numerous other variations and alternative arrangements may be devised by those skilled in the art without departing from the spirt and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments are meant to be illustrative only and should not be construed to be limiting in any manner.

What is claimed is:

1. A method comprising:
   generating a background mask as a function of at least one background image, wherein the at least one background image includes a blood vessel of interest;
   generating a contrast mask as a function of at least one contrast image, wherein the at least one contrast image includes a contrast agent within the blood vessel of interest;
   receiving a guidewire image, wherein the guidewire image includes a guidewire within the blood vessel of interest;
   linearizing the background mask, the contrast mask, and the guidewire image, wherein the linearizing comprises applying a logarithmic function, a polynomial function or a linear-logarithm function, wherein a linear function is used on a smaller signal and a logarithm function is used on a larger signal;

generating a roadmap image as a function of the linearized background mask, the linearized contrast mask, the linearized guidewire image, and a weighing factor, wherein the weighing factor is determined as a function of a patient parameter, wherein the patient parameter comprises a patient thickness or a patient weight, and wherein the roadmap image includes the blood vessel of interest and the guidewire; and outputting the roadmap image to a display;

wherein generating the roadmap comprises subtracting the linearized background mask from the linearized contrast mask; and subtracting the linearized background mask from the linearized guidewire image.

2. The method of claim 1, wherein the roadmap image is a live image.

3. The method of claim 1, wherein the guidewire and the blood vessel of interest contrast from one another in the roadmap image.

4. The method of claim 1, wherein the contrast agent is carbon dioxide.

5. The method of claim 1, wherein the guidewire image is a live image.

6. The method of claim 1, wherein an X-ray angiographic imaging device generate the at least one background image, the at least one contrast image, and the guidewire images.

7. The method of claim 6, wherein the X-ray angiographic imaging device generates a plurality of background images and a plurality of contrast images that include the blood vessel of interest, and wherein the plurality of background images includes neither the guidewire nor the contrast agent.

8. A system comprising:
an X-ray imaging device;
a processor; and
a computer readable storage medium in communication with the processor, wherein the processor executes computer readable instructions stored in the computer readable storage medium which cause the processor to:
generate a background mask as a function of at least one background image generated by the X-ray imaging device, wherein the at least one background image is acquired with no contrast injection nor guidewire inside the blood vessel;
generate a contrast mask as a function of at least one contrast image generated by the X-ray imaging device, wherein the at least one contrast image includes a contrast agent within the blood vessel of interest;
receive a guidewire image generated by the X-ray imaging device, wherein the guidewire image includes a guidewire within the blood vessel of interest;
linearize the background mask, the contrast mask, and the guidewire image, wherein the linearizing comprises applying a logarithmic function, a polynomial function or a linear-logarithm function, wherein a linear function is used on a smaller signal and a logarithm function is used on a larger signal;
generate a roadmap image as a function of the linearized background mask, the linearized contrast mask, the linearized guidewire image, and a weighting factor, wherein the weighting factor is determined as a function of a patient parameter, wherein the patient parameter comprises a patient thickness or a patient weight, and wherein the roadmap image includes the blood vessel of interest, and the guidewire; and
output the roadmap image to a display;
wherein generating the roadmap image comprises subtracting the linearized background mask from the linearized contrast mask; and subtracting the linearized background mask from the linearized guidewire image.

9. The system of claim 8, wherein the guidewire image and the roadmap image are live images.

10. The system of claim 8, wherein the guidewire and the blood vessel of interest contrast from one another in the roadmap image.

11. The system of claim 8, wherein the contrast agent is carbon dioxide.

12. A computer readable storage medium with computer readable instructions that, when executed by a processor, cause the processor to:
generate a live roadmap image as a function of a linearized background mask that includes a background of a blood vessel of interest; a linearized contrast mask that includes a contrast agent within the blood vessel of interest; a linearized live guidewire image; and a weighting factor, wherein the weighting factor is determined as a function of a patient parameter, wherein the patient parameter comprises a patient thickness or a patient weight, and wherein the weighting factor optionally increases with a patent thickness or a patient weight; and
output the roadmap image to a display wherein the background mask, the contrast mask, and the live guidewire image are linearized by applying a logarithmic function, a polynomial function or a linear-logarithm function, wherein a linear function is used on a smaller signal and a logarithm function is used on a larger signal; and
wherein generating the live roadmap image comprises subtracting the linearized background mask from the linearized contrast mask; and subtracting the linearized background mask from the linearized live guidewire image.

13. The computer readable storage medium of claim 12, wherein the contrast is carbon dioxide.

14. The computer readable storage medium of claim 13, wherein the guidewire and the blood vessel of interest contrast in the roadmap image.

* * * * *